US012586189B2

(12) United States Patent
Kim et al.

(10) Patent No.: US 12,586,189 B2
(45) Date of Patent: Mar. 24, 2026

(54) SYSTEM AND METHOD FOR VISUALIZING ANALYSIS RESULT OF ENDOSCOPIC IMAGE

(71) Applicant: WAYCEN INC., Seoul (KR)

(72) Inventors: Kyung Nam Kim, Suwon-si (KR); Jisoo Keum, Yongin-si (KR); Sangil Oh, Seoul (KR); Ju Yeon Choi, Seoul (KR); Pil Joo Kim, Seoul (KR)

(73) Assignee: WAYCEN INC., Seoul (KR)

( * ) Notice: Subject to any disclaimer, the term of this patent is extended or adjusted under 35 U.S.C. 154(b) by 377 days.

(21) Appl. No.: 18/525,159

(22) Filed: Nov. 30, 2023

(65) Prior Publication Data

US 2025/0045913 A1     Feb. 6, 2025

(30) Foreign Application Priority Data

Aug. 3, 2023   (KR) ........................ 10-2023-0101367
Nov. 23, 2023  (KR) ........................ 10-2023-0164619

(51) Int. Cl.
  *G06T 7/00*      (2017.01)
  *A61B 1/00*      (2006.01)
(52) U.S. Cl.
  CPC ...... *G06T 7/0012* (2013.01); *A61B 1/000096* (2022.02); *G06T 2207/10068* (2013.01); *G06T 2207/20076* (2013.01)

(58) Field of Classification Search
  CPC .................................................... G06T 7/0012
  See application file for complete search history.

(56) References Cited

U.S. PATENT DOCUMENTS

2021/0153808 A1* 5/2021 Tada ...................... A61B 6/032
2022/0406035 A1* 12/2022 Keum .................. G06V 10/764
2023/0368423 A1* 11/2023 Wu ............................ G06T 7/73
2024/0420461 A1* 12/2024 Saalbach ............... G06V 10/25

* cited by examiner

*Primary Examiner* — Benjamin O Dulaney
(74) *Attorney, Agent, or Firm* — Paratus Law Group, PLLC

(57) ABSTRACT

A method of visualizing an analysis result of an endoscopic image according to a first embodiment includes loading, by a model loading/condition setting unit, a plurality of analysis models and setting analysis conditions, analyzing, by an image analyzer, the image using the plurality of analysis models when the situation requires image analysis, extracting, by an AM extractor/generator, AMs of the plurality of analysis models and generating a CAM when an image analysis result satisfies a set analysis condition, generating an ACAM by applying weights to CAMs extracted in previous and current image frames, extracting a peak activation value from the ACAM by an activation value extractor, and extracting, by a closed curve extractor, a closed curve of an AM and drawing the closed curve on a corresponding analysis image when the peak activation value is greater than or equal to a threshold.

18 Claims, 6 Drawing Sheets

FIG. 4

SYSTEM AND METHOD FOR VISUALIZING ANALYSIS RESULT OF ENDOSCOPIC IMAGE

CROSS-REFERENCE TO PRIOR APPLICATIONS

This application claims priority to Korean Patent Application Nos. 10-2023-0101367 (filed Aug. 3, 2023) and 10-2023-0164619 (filed Nov. 23, 2023), which are all hereby incorporated by reference in their entirety.

BACKGROUND

The present invention relates to a system and method for visualizing an analysis result of an endoscopic image, and more particularly to a system and method for visualizing an analysis result of an endoscopic image that selects the analysis result of the endoscopic image using a plurality of artificial intelligence models and visualizes a final result.

When detecting a target by analyzing an endoscopic image using an endoscopic image analysis AI (Artificial Intelligence) model, if the analysis target is detected based on a result of analyzing a single frame, it is possible to determine that the target is detected. In this instance, accuracy of detection may decrease when only a single frame result is used due to movement of an endoscope or incorrect detection (FP, false positive).

As an alternative to the above problems, a method has been proposed to confirm that the analysis target is detected when the analysis target is continuously detected in a fixed number of frames, N. However, a processing speed of an endoscopic image analysis device may vary depending on manufacturers, and setting of a fixed number of frames N may affect detection accuracy according to a movement speed of an examiner operating the endoscope.

Endoscopic analysis software including a model based on object detection may output coordinates as a result and display the coordinates in the form of a square. In this instance, as a post-processing method for reducing false detection, when the analysis target is continuously detected in N frames, the analysis target is displayed on a screen. Even when the endoscope analysis software includes a plurality of object detection models, there are limitations in indicating a detailed target area using output in the form of square coordinates.

SUMMARY

The present invention has been created in consideration of the above matters, and an object of the present invention is to provide a system and method for visualizing an analysis result of an endoscopic image capable of primarily reducing a possibility of occurrence of false detection predicted in each model by determining whether an analysis target is detected using an agree-all or voting method for probability values predicted by a plurality of models, and capable of secondarily reducing a possibility of false detection by extracting a common activation map (CAM) of an agree-all or voting model for a current frame.

Another object of the present invention is to provide a system and method for visualizing an analysis result of an endoscopic image capable of thirdly reducing a possibility of false detection by applying weights to CAMs extracted from a previous frame and a current frame to extract an adjacent common activation map (ACAM), and capable of fourthly reducing a possibility of false detection by determining whether a peak activation value of the ACAM is greater than or equal to a detection confirmation threshold.

Still another object of the present invention is to provide a system and method for visualizing an analysis result of an endoscopic image capable of minimizing false detection using a plurality of models and allowing a predicted analysis target to be indicated in detail in the form of a closed curve, and capable of selecting a representative image from an analysis result using an ACAM in a representative image selection process.

To achieve the above objects, a system for visualizing an analysis result of an endoscopic image according to the present invention includes a model loading/condition setting unit configured to load a plurality of analysis models and set analysis conditions of the analysis models, an image analyzer configured to determine whether a situation requires image analysis, and to read an image frame and analyze the image using the plurality of analysis models when the situation requires image analysis, an activation map (AM) extractor/generator configured to determine whether an image analysis result by the image analyzer satisfies an analysis condition set by the model loading/condition setting unit, extract AMs of the plurality of analysis models when the analysis condition is satisfied, generate a CAM based on the extracted AMs, determine whether an analysis target is detected in a previous image frame, and generate an ACAM by applying weights to CAMs extracted in the previous image frame and a current image frame when the analysis target is detected, an activation value extractor configured to extract a peak activation value from the ACAM generated by the AM extractor/generator, a closed curve extractor configured to determine whether the extracted peak activation value is greater than or equal to a detection confirmation threshold, extract a closed curve of an AM when the extracted peak activation value is greater than or equal to the detection confirmation threshold, and draw the closed curve on a corresponding analysis image, and a controller configured to check conditions and controls operations of the model loading/condition setting unit, the image analyzer, the AM extractor/generator, the activation value extractor, and the closed curve extractor, transmit a control command allowing performance of a function of each of the model loading/condition setting unit, the image analyzer, the AM extractor/generator, the activation value extractor, and the closed curve extractor, and read, from a database DB, and provide data, information and an application necessary to perform each function or store the data, information and application in the database DB.

When the AM extractor/generator generates the ACAM, the AM extractor/generator may generate the ACAM by a method using an agree-all model or a method using a voting model.

The method using the agree-all model may set each of analysis conditions of the plurality of analysis models to a specific predicted probability value.

The method using the voting model may set each of the analysis conditions of the plurality of analysis models to a specific predicted probability value different from the specific predicted probability value in the method using the agree-all model.

The system may further include a representative image selector configured to select a representative image through measurement of a similarity with respect to the ACAM.

When the representative image selector selects the representative image, an output probability of a frame having a highest similarity may be used as a probability of the representative image, or an output probability average value of representative image candidates greater than or equal to a threshold may be used as the probability of the representative image.

To achieve the above objects, a method of visualizing an analysis result of an endoscopic image according to a first embodiment of the present invention includes a) loading, by a model loading/condition setting unit, a plurality of analysis models and setting analysis conditions of the analysis models, b) determining, by an image analyzer, whether a situation requires image analysis, and reading an image frame and analyzing the image using the plurality of analysis models when the situation requires image analysis, c) determining, by an AM extractor/generator, whether an image analysis result by the image analyzer satisfies an analysis condition set by the model loading/condition setting unit, d) extracting, by the AM extractor/generator, AMs of the plurality of analysis models when the analysis condition is satisfied in the determining of the step c) and generating a CAM based on the extracted AMs, e) determining, by the AM extractor/generator, whether an analysis target is detected in a previous image frame and generating an ACAM by applying weights to CAMs extracted in the previous image frame and a current image frame when the analysis target is detected, f) extracting, by an activation value extractor, a peak activation value from the ACAM generated by the AM extractor/generator, and g) determining, by a closed curve extractor, whether the extracted peak activation value is greater than or equal to a detection confirmation threshold, extracting a closed curve of an AM when the extracted peak activation value is greater than or equal to the detection confirmation threshold, and drawing the closed curve on a corresponding analysis image.

When the AM extractor/generator generates the ACAM in the step e), the AM extractor/generator may generate the ACAM by a method using an agree-all model or a method using a voting model.

The method using the agree-all model may set each of analysis conditions of the plurality of analysis models to a specific predicted probability value.

The method using the voting model may set each of analysis conditions of the plurality of analysis models to a specific predicted probability value different from the specific predicted probability value in the method using the agree-all model.

The method may further include selecting, by a representative image selector, a representative image through measurement of a similarity with respect to the ACAM after the step e).

When the representative image selector selects the representative image, an output probability of a frame having a highest similarity may be used as a probability of the representative image, or an output probability average value of representative image candidates greater than or equal to a threshold may be used as the probability of the representative image.

To achieve the above objects, a method of visualizing an analysis result of an endoscopic image according to a second embodiment of the present invention includes m) loading, by a model loading/condition setting unit, a plurality of analysis models and setting analysis conditions of the analysis models, n) determining, by an image analyzer, whether a situation requires image analysis, and reading an image frame when the situation requires image analysis, o) determining, by the image analyzer, whether a mode is a detection mode or a classification mode, analyzing the image in the detection mode when the mode is the detection mode, and analyzing the image in the classification mode when the mode is the classification mode, p) determining, by an AM extractor/generator, whether an image analysis result by the image analyzer satisfies an analysis condition set by the model loading/condition setting unit, q) extracting, by the AM extractor/generator, AMs of the plurality of analysis models when the analysis condition is satisfied in the determining of the step d) and generating a CAM based on the extracted AMs, r) determining, by the AM extractor/generator, whether an analysis target is detected in a previous image frame and generating an ACAM by applying weights to CAMs extracted in the previous image frame and a current image frame when the analysis target is detected, s) extracting, by an activation value extractor, a peak activation value from the ACAM generated by the AM extractor/generator, t) determining, by a closed curve extractor, whether the extracted peak activation value is greater than or equal to a detection confirmation threshold, extracting a closed curve of an AM when the extracted peak activation value is greater than or equal to the detection confirmation threshold, and drawing the closed curve on a corresponding analysis image, and u) determining, by the image analyzer, whether to change an analysis mode, and changing the analysis mode to the classification mode when a current analysis mode is the detection mode and changing the analysis mode to the detection mode when the current analysis mode is the classification mode in a case of changing the analysis mode.

When the AM extractor/generator generates the ACAM in the step r), the AM extractor/generator may generate the ACAM by a method using an agree-all model or a method using a voting model.

The method using the agree-all model may set each of analysis conditions of the plurality of analysis models to a specific predicted probability value.

The method using the voting model may set each of analysis conditions of the plurality of analysis models to a specific predicted probability value different from the specific predicted probability value in the method using the agree-all model.

The method may further include selecting, by a representative image selector, a representative image through measurement of a similarity with respect to the ACAM after the step r).

When the representative image selector selects the representative image, an output probability of a frame having a highest similarity may be used as a probability of the representative image, or an output probability average value of representative image candidates greater than or equal to a threshold may be used as the probability of the representative image.

According to the present invention described above, there is an advantage of reducing a possibility of false detection through four steps by determining whether an analysis target is detected using a plurality of analysis models, extracting a CAM of an agree-all or voting model for a current frame, applying weights to CAMs extracted in a previous frame and the current frame to extract an ACAM, and determining whether a peak activation value of the ACAM is greater than or equal to a detection confirmation threshold.

In addition, there are advantages of being able to indicate an analysis target predicted using a plurality of analysis models in detail in the form of a closed curve, and to select a representative image from an analysis result using an ACAM in a representative image selection process.

BRIEF DESCRIPTION OF THE DRAWINGS

FIG. 4 is a diagram illustrating an overview of generating CAMs of adjacent frames using a voting method in the method of visualizing an analysis result of an endoscopic image according to the present invention.

DETAILED DESCRIPTION

Hereinafter, embodiments of the present invention will be described in detail with reference to the attached drawings.

Figure 1:
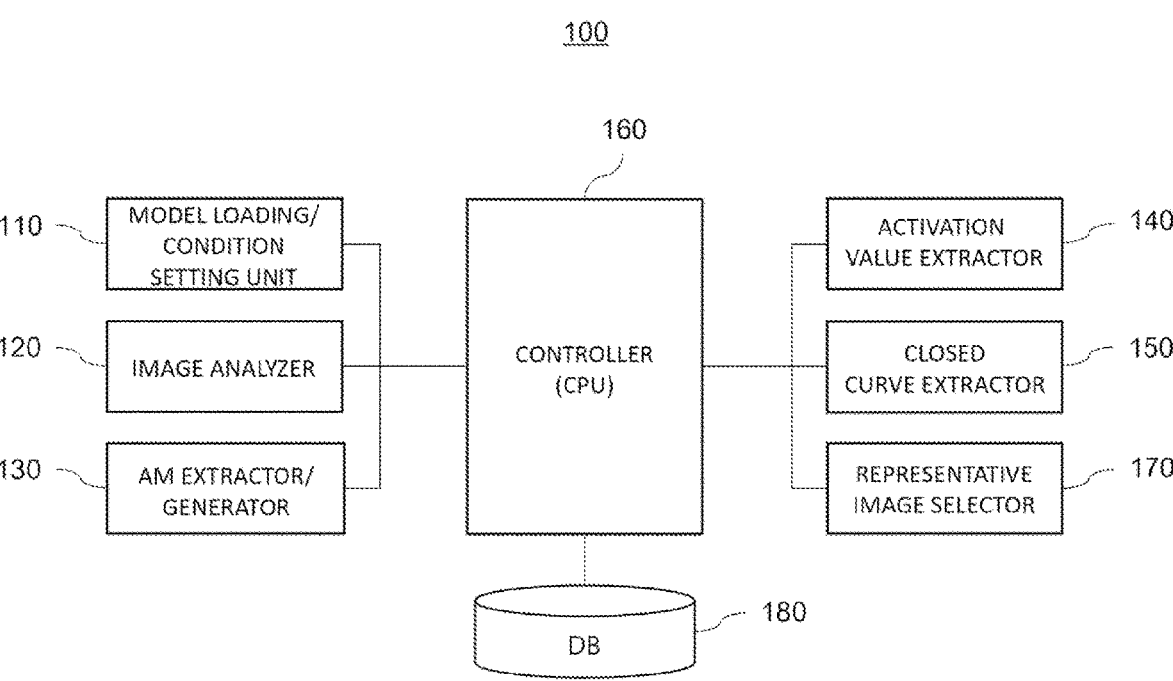
FIG. 1 is a diagram schematically illustrating a configuration of a system for visualizing an analysis result of an endoscopic image according to the present invention.

FIG. 1 is a diagram schematically illustrating a configuration of a system for visualizing an analysis result of an endoscopic image according to an embodiment of the present invention.

Referring to FIG. 1, a system 100 for visualizing an analysis result of an endoscopic image according to the present invention may include a model loading/condition setting unit 110, an image analyzer 120, an AM extractor/generator 130, an activation value extractor 140, a closed curve extractor 150, and a controller 160.

The model loading/condition setting unit 110 loads a plurality of (for example, four) analysis models (see FIGS. 3 and 4) and sets analysis conditions of the analysis models (for example, a predicted probability value of 0.8 or more or predicted probability values of 0.85 or more in three models).

The image analyzer 120 determines whether a situation requires image analysis. When the situation requires image analysis, the image analyzer 120 reads an image frame and analyzes the image using the plurality of analysis models.

The AM extractor/generator 130 determines whether an image analysis result by the image analyzer 120 satisfies an analysis condition set by the model loading/condition setting unit 110. When the analysis condition is satisfied, the AM extractor/generator 130 extracts AMs of the plurality of analysis models (see FIGS. 3 and 4), generates a CAM based on the extracted AMs, and determines whether an analysis target is detected in a previous image frame. When the analysis target is detected, the AM extractor/generator 130 generates an ACAM by applying weights to CAMs extracted in the previous image frame and a current image frame. Here, when the AM extractor/generator 130 generates the ACAM, the AM extractor/generator 130 may generate the ACAM by a method using an agree-all model or a method using a voting model. In this instance, in the method using the agree-all model, each of analysis conditions of the plurality of analysis models may be set to a specific predicted probability value (for example, the plurality of analysis models is all set to a predicted probability value 0.8 or more). In this instance, further, in the method using the voting model, each of analysis conditions of the plurality of analysis models may be set to a specific predicted probability value different from the specific predicted probability value in the method using the agree-all model (for example, predicted probability values of three analysis models are 0.85 or more). Here, the specific predicted probability value serving as each analysis condition in the method using the agree-all model and the method using the voting model described above is not limited to being fixed to any one value, and may be set to various values depending on the target or situation to which the analysis condition is applied.

The activation value extractor 140 extracts a peak activation value from the ACAM generated by the AM extractor/generator 130.

The closed curve extractor 150 determines whether the extracted peak activation value is greater than or equal to a detection confirmation threshold, extracts a closed curve of an AM when the extracted peak activation value is greater than or equal to the detection confirmation threshold, and draws the closed curve on the corresponding analysis image.

The controller 160 checks conditions and controls operations of the model loading/condition setting unit 110, the image analyzer 120, the AM extractor/generator 130, the activation value extractor 140, and the closed curve extractor 150, transmits a control command allowing performance of a function of each of the model loading/condition setting unit 110, the image analyzer 120, the AM extractor/generator 130, the activation value extractor 140, and the closed curve extractor 150, and reads, from a database DB 180, and provides data, information and an application necessary to perform each function or stores the data, information and application in the database DB 180. Here, the database DB 180 stores and manages various software programs for system operation, or data or information necessary for the model loading/condition setting unit 110, the image analyzer 120, the AM extractor/generator 130, the activation value extractor 140, and the closed curve extractor 150 to perform functions related to model loading, condition setting, image analysis, AM extraction and generation, activation value extraction, or closed curve extraction or process operations.

The system 100 for visualizing an analysis result of an endoscopic image according to the present invention having the above configuration may further include a representative image selector 170 configured to select a representative image through measurement of a similarity with respect to the ACAM. In this instance, when the representative image selector 170 selects the representative image, an output probability of a frame having a highest similarity may be used as a probability of the representative image, or an output probability average value of representative image candidates greater than or equal to a threshold may be used as the probability of the representative image. A description related thereto will be given later.

Here, further, the model loading/condition setting unit 110, the image analyzer 120, the AM extractor/generator 130, the activation value extractor 140, the closed curve extractor 150, the controller 160, the representative image selector 170, and the database DB 180 may be integrated as a whole and configured as one computer system.

A description will hereinafter be given of a method of visualizing an analysis result of an endoscopic image based on the system for visualizing an analysis result of an endoscopic image according to the present invention having the above configuration.

Figure 2:
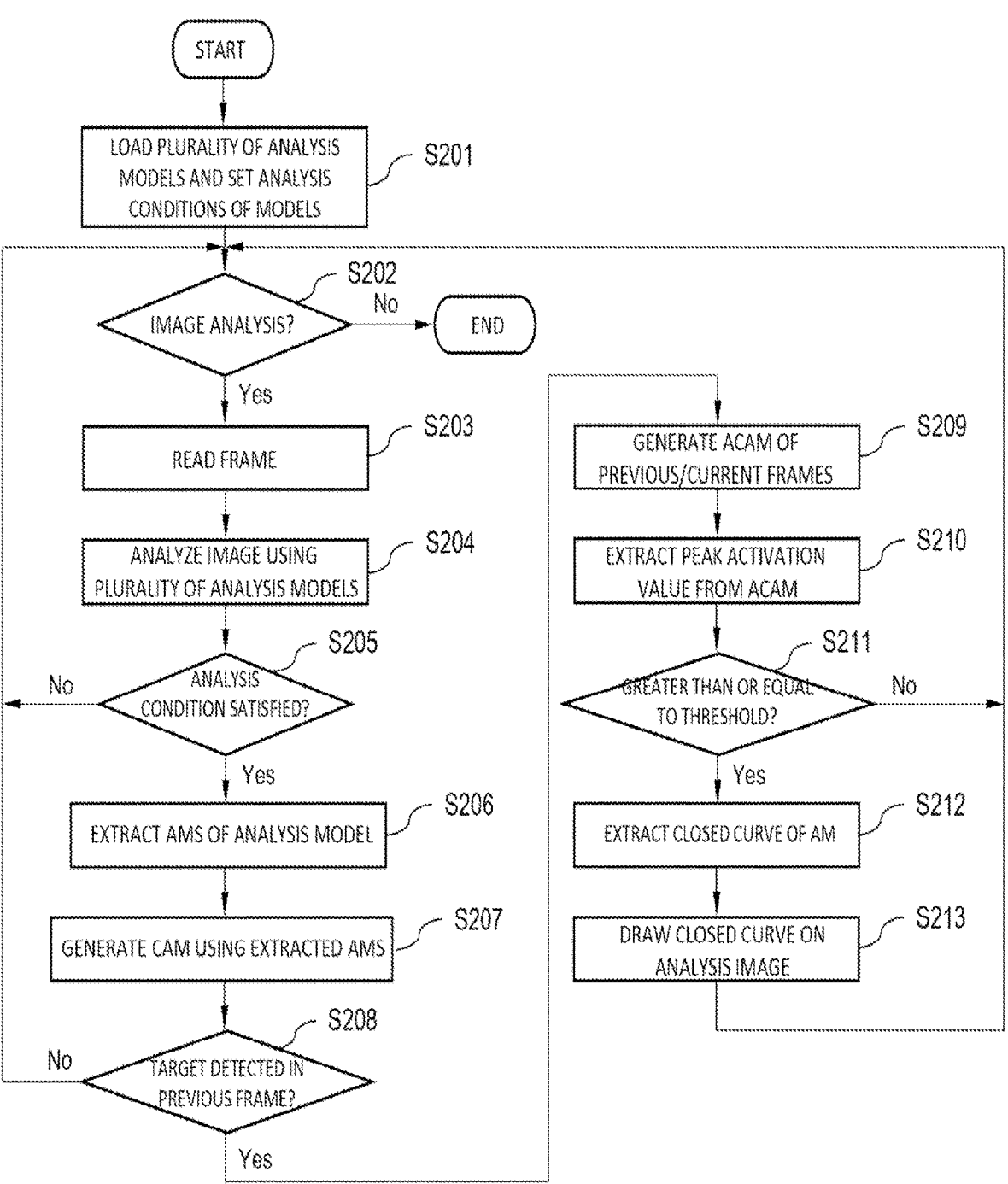
FIG. 2 is a flowchart illustrating an execution process of a method of visualizing an analysis result of an endoscopic image according to a first embodiment of the present invention.

FIG. 2 is a flowchart illustrating an execution process of the method of visualizing an analysis result of an endoscopic image according to a first embodiment of the present invention.

Referring to FIG. 2, in the method of visualizing an analysis result of an endoscopic image according to the first embodiment of the present invention, first, the model loading/condition setting unit 110 loads a plurality of (for example, four) (see FIGS. 3 and 4) analysis models, and sets analysis conditions of the analysis models (step S201). For example, each of the analysis conditions may be set to a predicted probability value of 0.8 or more or a predicted probability value of 0.85 or more in three models.

When loading of the analysis models and setting of the analysis conditions are completed in this way, the image analyzer 120 determines whether a situation requires image analysis (step S202), reads an image frame when image analysis is required, and analyzes the image using the plurality of analysis models (steps S203 and S204).

Then, the AM extractor/generator 130 determines whether an image analysis result by the image analyzer 120 satisfies the analysis conditions set by the model loading/condition setting unit 110 (step S205).

When the analysis conditions are satisfied in determination of step S205, the AM extractor/generator 130 extracts AMs (see FIGS. 3 and 4) of the plurality of analysis models (step S206), and generates a CAM based on the extracted AMs (step S207).

In addition, the AM extractor/generator 130 determines whether an analysis target (for example, a certain lesion such as stomach cancer) is detected in a previous image frame (frame N−1) (see FIGS. 3 and 4) (step S208), and when the analysis target is detected, the AM extractor/generator 130 generates an ACAM by applying weights to CAMs extracted in the previous image frame and the current image frame (step S209). Here, when the AM extractor/generator 130 generates the ACAM as above, the ACAM may be generated using the method using the agree-all model (see FIG. 3) or the method using the voting model (see FIG. 4). In this instance, the method using the agree-all model may set each of the analysis conditions of the plurality of analysis models to a specific predicted probability value (for example, a predicted probability value of 0.8 or more in all the plurality of analysis models). In this instance, further, the method using the voting model may set each of the analysis conditions of the plurality of analysis models to a specific predicted probability value (for example, a predicted probability value of 0.85 or more in three analysis models) different from the specific predicted probability value in the method using the agree-all model. Here, the specific predicted probability value serving as each analysis condition in the method using the agree-all model and the method using the voting model described above is not limited to being fixed to any one value, and may be set to various values depending on the target or situation to which the analysis condition is applied. Here, generation of the ACAM using the agree-all model and the voting model will be described again below.

When the ACAM is generated in this way, the activation value extractor 140 extracts a peak activation value from the ACAM generated by the AM extractor/generator 130 (step S210).

Thereafter, the closed curve extractor 150 determines whether the extracted peak activation value is greater than or equal to the detection confirmation threshold (step S211), and extracts a closed curve of the AM and draws the closed curve in the corresponding analysis image when the value is greater than or equal to the threshold (steps S212 and S213). In this way, the analysis result of the endoscopic image is visualized, thereby allowing the analysis target predicted using the plurality of analysis models to be indicated in detail in the form of a closed curve.

Meanwhile, in the series of processes described above, after step S209, the representative image selector 170 may further include a step of selecting a representative image through measurement of a similarity with respect to the ACAM.

In this instance, when the representative image selector 170 selects a representative image, an output probability of a frame having a highest similarity may be used as a probability of the representative image, or an output probability average value of representative image candidates greater than or equal to a threshold may be used as the probability of the representative image. A description related thereto will be given later.

Figure 3:
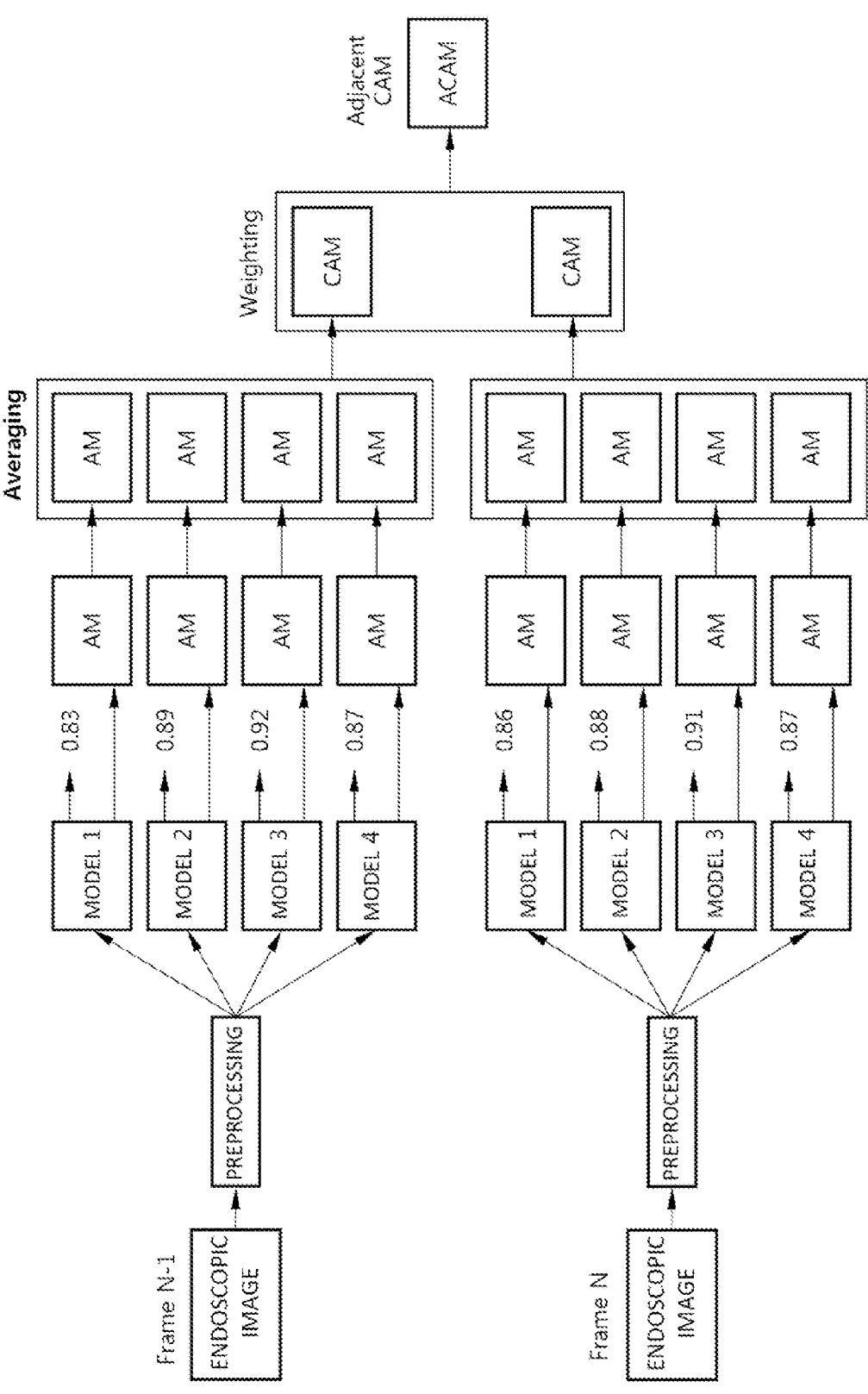
FIG. 3 is a diagram illustrating an overview of generating CAMs of adjacent frames using an agree-all method in the method of visualizing an analysis result of an endoscopic image according to the present invention.

FIG. 3 is a diagram illustrating an overview of generating CAMs of adjacent frames using an agree-all method in the method of visualizing an analysis result of an endoscopic image according to the present invention.

Referring to FIG. 3, the AM extractor/generator 130 first preprocesses an endoscopic image of each of a previous image frame (Frame N−1) and a current image frame (Frame N), and then extracts AMs of a plurality of analysis models (for example, four models of model 1 to model 4). In this instance, an analysis condition of each analysis model may be set to a predicted probability value of 0.8 or more. FIG. 3 illustrates that predicted probability values of model 1, model 2, model 3, and mode 4 are 0.83, 0.89, 0.92, and 0.87, respectively, in the case of the previous image frame (Frame N−1), and that predicted probability values of model 1, model 2, model 3, and mode 4 are 0.86, 0.88, 0.91, and 0.87, respectively, in the case of the current image frame (Frame N).

When AMs are extracted in this way, the AM extractor/generator 130 obtains an average value of the predicted probability values of the plurality of (four) AMs of each of the previous image frame (Frame N−1) and the current image frame (Frame N), and generates a CAM of each of the previous image frame (Frame N−1) and the current image frame (Frame N) each having the average value based on the AMs of each of the image frames.

Then, an ACAM is generated by applying a weight to each of the CAMs extracted from the previous image frame (Frame N−1) and the current image frame (Frame N), respectively.

Figure 4:
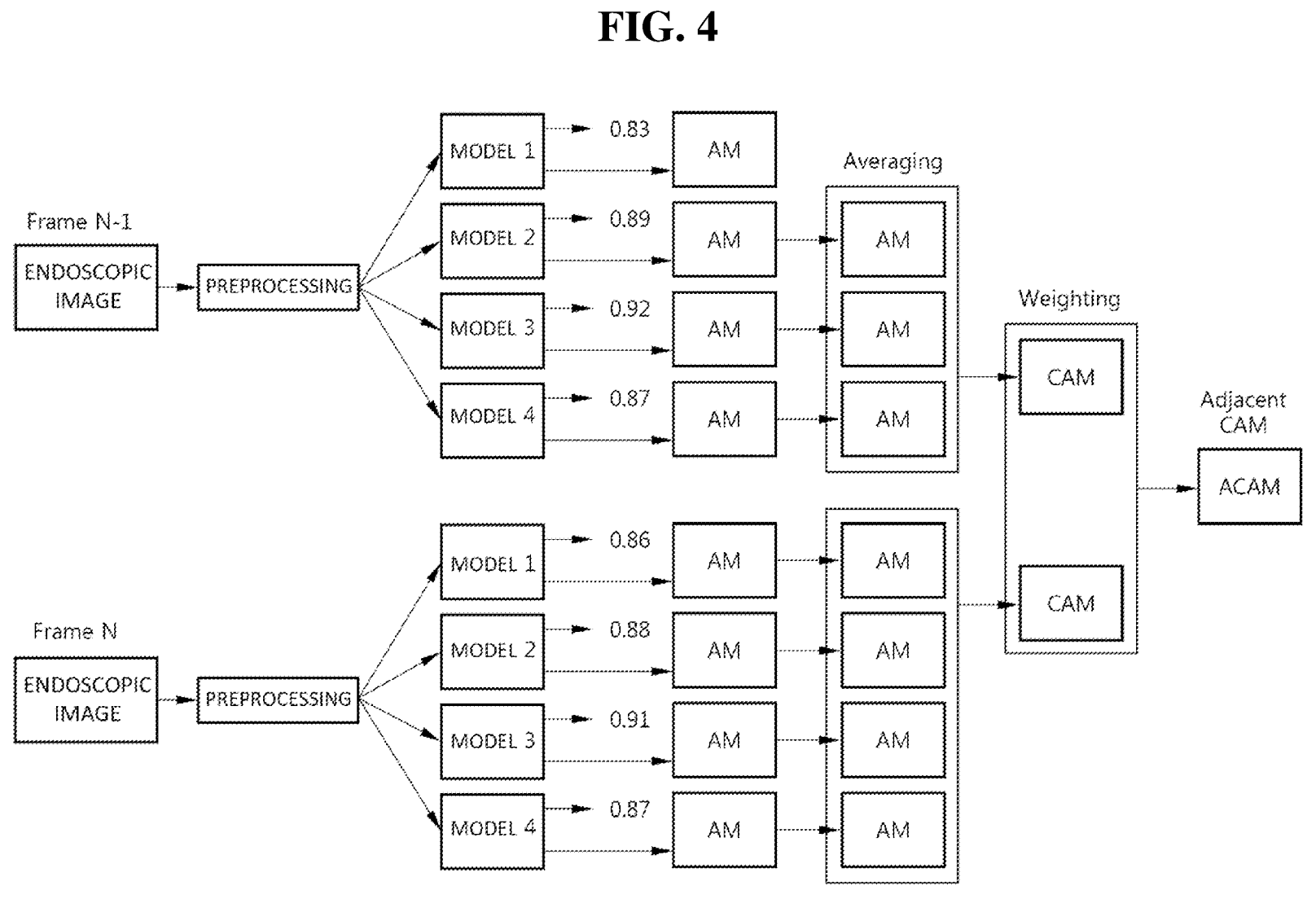

FIG. 4 is a diagram illustrating an overview of generating CAMs of adjacent frames using a voting method in the method of visualizing an analysis result of an endoscopic image according to the present invention.

Referring to FIG. 4, this process is practically the same as the process of generating CAMs of adjacent frames using the agree-all method described above with reference to FIG. 3. Therefore, a description of the process of generating CAMs of adjacent frames will be replaced with the above description with reference to FIG. 3, and only a difference from the agree-all method described above will be described.

In this voting method, the analysis condition of each analysis model is set differently from the analysis condition of the agree-all method described above. In other words, this voting method (the method using the voting model) is different in that each of the analysis conditions of the plurality of analysis models is set to a different specific predicted probability value (for example, a predicted probability value of 0.85 or more in three analysis models) from a specific predicted probability value (a predicted probability value of 0.8 or more) in the above-described agree-all method (the method using the agree-all model). FIG. 4 illustrates that predicted probability values of model 1, model 2, model 3, and mode 4 are 0.83, 0.89, 0.92, and 0.87, respectively, in the case of the previous image frame (Frame N−1), and illustrates that an AM of model 1 having the predicted probability value of 0.83 is discarded and only AMs of the remaining three analysis models (model 2 to model 4) each having the predicted probability value of 0.85 or more are taken according to the analysis conditions (a predicted probability value of 0.85 or more in three analysis models).

Figure 5:
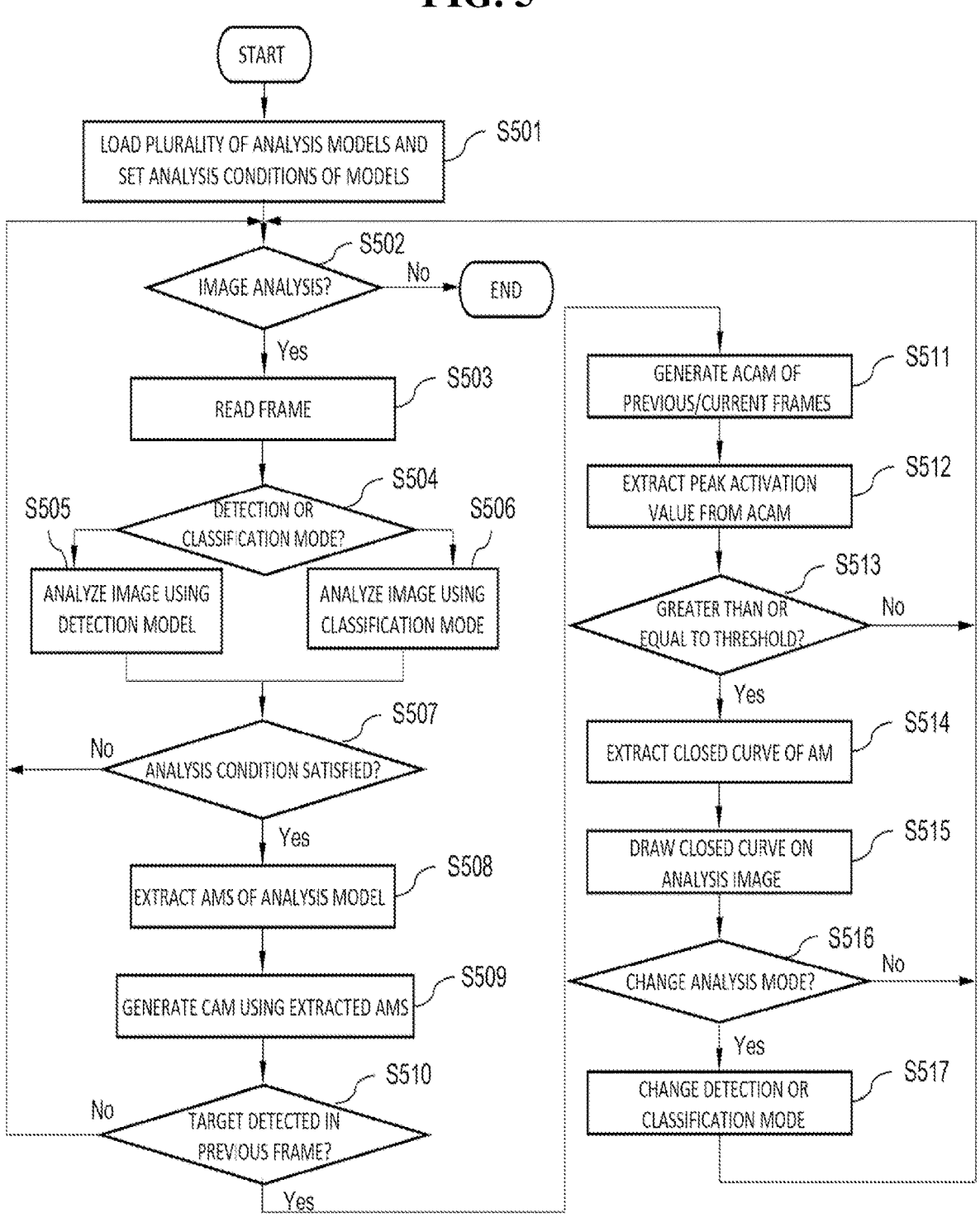
FIG. 5 is a flowchart illustrating an execution process of a method of visualizing an analysis result of an endoscopic image according to a second embodiment of the present invention.

FIG. 5 is a flowchart illustrating an execution process of a method of visualizing an analysis result of an endoscopic image according to a second embodiment of the present invention.

Referring to FIG. 5, in the method of visualizing an analysis result of an endoscopic image according to the second embodiment of the present invention, first, the model loading/condition setting unit 110 loads a plurality of (for example, four) (see FIGS. 3 and 4) analysis models, and sets analysis conditions of the analysis models (step S501). For example, each of the analysis conditions may be set to a predicted probability value of 0.8 or more or a predicted probability value of 0.85 or more in three models.

When loading of the analysis models and setting of the analysis conditions are completed in this way, the image analyzer 120 determines whether a situation requires image analysis (step S502), and reads an image frame when image analysis is required (step S503).

Further, the image analyzer 120 determines whether a mode is a detection mode or a classification mode (step S504). When the mode is the detection mode, the image analyzer 120 analyzes the image using a detection model (step S505) and analyzes the image using a classification model when the mode is the classification mode (step S506).

Then, the AM extractor/generator 130 determines whether an image analysis result by the image analyzer 120 satisfies an analysis condition set by the model loading/condition setting unit 110 (step S507).

When the analysis conditions are satisfied in determination of step S507, the AM extractor/generator 130 extracts AMs (see FIGS. 3 and 4) of the plurality of analysis models (step S508), and generates a CAM based on the extracted AMs (step S509).

In addition, the AM extractor/generator 130 determines whether an analysis target (for example, a certain lesion such as stomach cancer) is detected in a previous image frame (frame N−1) (see FIGS. 3 and 4) (step S510), and when the analysis target is detected, the AM extractor/generator 130 generates an ACAM by applying weights to CAMs extracted in the previous image frame and the current image frame (step S511). Here, when the AM extractor/generator 130 generates the ACAM as above, the ACAM may be generated using the method using the agree-all model (see FIG. 3) or the method using the voting model (see FIG. 4). In this instance, the method using the agree-all model may set each of the analysis conditions of the plurality of analysis models to a specific predicted probability value (for example, a predicted probability value of 0.8 or more in all the plurality of analysis models). In this instance, further, the method using the voting model may set each of the analysis conditions of the plurality of analysis models to a specific predicted probability value (for example, a predicted probability value of 0.85 or more in three analysis models) different from the specific predicted probability value in the method using the agree-all model. Here, the specific predicted probability value serving as each analysis condition in the method using the agree-all model and the method using the voting model described above is not limited to being fixed to any one value, and may be set to various values depending on the target or situation to which the analysis condition is applied.

When the ACAM is generated in this way, the activation value extractor 140 extracts a peak activation value from the ACAM generated by the AM extractor/generator 130 (step S512).

The closed curve extractor 150 determines whether the extracted peak activation value is greater than or equal to the detection confirmation threshold (step S513), and extracts a closed curve of the AM and draws the closed curve in the corresponding analysis image when the value is greater than or equal to the threshold (steps S514 and S515).

Thereafter, the image analyzer 120 determines whether to change an analysis mode (step S516). In the case of changing an analysis mode, the image analyzer 120 changes the analysis mode to the classification mode when the current analysis mode is the detection mode and changes the analysis mode to the detection mode when the current analysis mode is the classification mode (step S517).

In the series of processes described above, after step S511, the representative image selector 170 may further include a step of selecting a representative image through measurement of a similarity with respect to the ACAM.

In this instance, when the representative image selector 170 selects a representative image, an output probability of a frame having a highest similarity may be used as a probability of the representative image, or an output probability average value of representative image candidates greater than or equal to the threshold may be used as the probability of the representative image.

Figure 6:
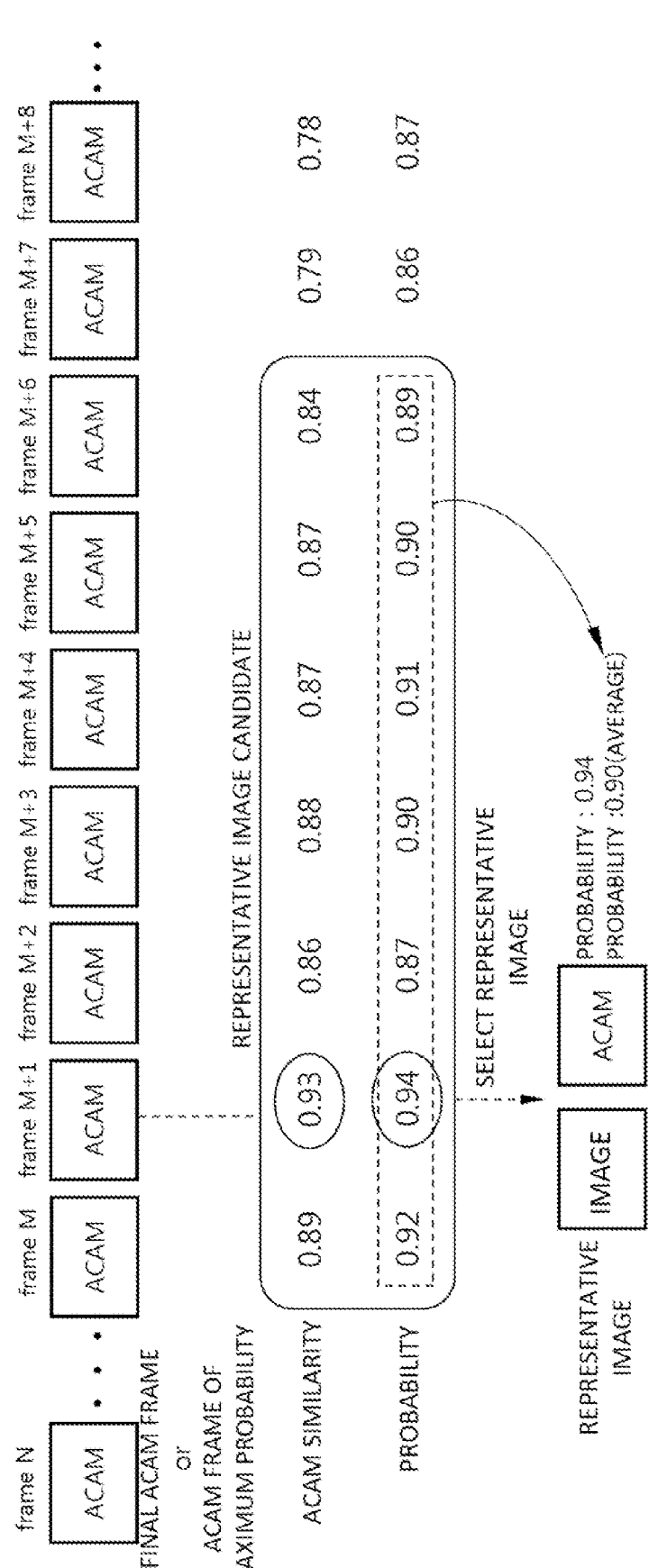
FIG. 6 is a diagram illustrating a process of selecting a representative image through measurement of a similarity with respect to a CAM of an adjacent frame in the method of visualizing an analysis result of an endoscopic image according to the present invention.

Meanwhile, FIG. 6 is a diagram illustrating a process of selecting a representative image through measurement of a similarity with respect to a CAM of an adjacent frame in the method of visualizing an analysis result of an endoscopic image according to the present invention. Referring to FIG. 6, when there are nine ACAM frames starting from an Mth frame (frame M) to an (M+1)th frame (frame M+1), . . . , an (M+8)th frame (frame M+8) as similar ACAM frames with respect to a final ACAM frame or an ACAM frame of a maximum probability as a current frame (frame N), it is assumed that ACAM similarities of the respective frames are 0.89, 0.93, 0.86, 0.88, 0.87, 0.87, 0.84, 0.79, and 0.78, and probabilities thereof are 0.92, 0.94, 0.87, 0.90, 0.91, 0.90, 0.89, 0.86, and 0.87.

In this instance, when the representative image selector 170 selects a representative image, an output probability (0.94) of a frame (frame M+1) having a highest similarity (similarity 0.93) may be used as a probability of the representative image among representative image candidates, or an output probability average value (0.90) of representative image candidates greater than or equal to a threshold may be used as the probability of the representative image.

As described above, the system and method for visualizing an analysis result of an endoscopic image according to the present invention has an advantage of reducing a possibility of false detection through four steps by determining whether an analysis target is detected using a plurality of analysis models, extracting a CAM of an agree-all or voting model for a current frame, applying weights to CAMs extracted in a previous frame and the current frame to extract an ACAM, and determining whether a peak activation value of the ACAM is greater than or equal to a detection confirmation threshold.

In addition, there are advantages of being able to indicate an analysis target predicted using a plurality of analysis models in detail in the form of a closed curve, and to select a representative image from an analysis result using an ACAM in a representative image selection process.

What is claimed is:

1. A system for visualizing an analysis result of an endoscopic image, the system comprising:

a model loading/condition setting unit configured to load a plurality of analysis models and set analysis conditions of the analysis models;

an image analyzer configured to determine whether a situation requires image analysis, and to read an image frame and analyze the image using the plurality of analysis models when the situation requires image analysis;

an activation map (AM) extractor/generator configured to determine whether an image analysis result by the image analyzer satisfies an analysis condition set by the model loading/condition setting unit, extract AMs of the plurality of analysis models when the analysis condition is satisfied, generate a common activation map (CAM) based on the extracted AMs, determine whether an analysis target is detected in a previous image frame, and generate an adjacent common activation map (ACAM) by applying weights to CAMs extracted in the previous image frame and a current image frame when the analysis target is detected;

an activation value extractor configured to extract a peak activation value from the ACAM generated by the AM extractor/generator;

a closed curve extractor configured to determine whether the extracted peak activation value is greater than or equal to a detection confirmation threshold, extract a closed curve of an AM when the extracted peak activation value is greater than or equal to the detection confirmation threshold, and draw the closed curve on a corresponding analysis image; and a controller configured to check conditions and controls operations of the model loading/condition setting unit, the image analyzer, the AM extractor/generator, the activation value extractor, and the closed curve extractor, transmit a control command allowing performance of a function of each of the model loading/condition setting unit, the image analyzer, the AM extractor/ generator, the activation value extractor, and the closed curve extractor, and read, from a database DB, and provide data, information and an application necessary to perform each function or store the data, information and application in the database DB.

2. The system according to claim 1, wherein, when the AM extractor/generator generates the ACAM, the AM extractor/generator generates the ACAM by a method using an agree-all model or a method using a voting model.

3. The system according to claim 2, wherein the method using the agree-all model sets each of analysis conditions of the plurality of analysis models to a specific predicted probability value.

4. The system according to claim 3, wherein the method using the voting model sets each of the analysis conditions of the plurality of analysis models to a specific predicted probability value different from the specific predicted probability value in the method using the agree-all model.

5. The system according to claim 1, further comprising a representative image selector configured to select a representative image through measurement of a similarity with respect to the ACAM.

6. The system according to claim 5, wherein, when the representative image selector selects the representative image, an output probability of a frame having a highest similarity is used as a probability of the representative image, or an output probability average value of representative image candidates greater than or equal to a threshold is used as the probability of the representative image.

7. A method of visualizing an analysis result of an endoscopic image, the method comprising steps of:

a) loading, by a model loading/condition setting unit, a plurality of analysis models and setting analysis conditions of the analysis models;

b) determining, by an image analyzer, whether a situation requires image analysis, and reading an image frame and analyzing the image using the plurality of analysis models when the situation requires image analysis;

c) determining, by an AM extractor/generator, whether an image analysis result by the image analyzer satisfies an analysis condition set by the model loading/condition setting unit;

d) extracting, by the AM extractor/generator, AMs of the plurality of analysis models when the analysis condition is satisfied in the determining of the step c) and generating a CAM based on the extracted AMs;

e) determining, by the AM extractor/generator, whether an analysis target is detected in a previous image frame and generating an ACAM by applying weights to CAMs extracted in the previous image frame and a current image frame when the analysis target is detected;

f) extracting, by an activation value extractor, a peak activation value from the ACAM generated by the AM extractor/generator; and g) determining, by a closed curve extractor, whether the extracted peak activation value is greater than or equal to a detection confirmation threshold, extracting a closed curve of an AM when the extracted peak activation value is greater than or equal to the detection confirmation threshold, and drawing the closed curve on a corresponding analysis image.

8. The method according to claim 7, wherein, when the AM extractor/generator generates the ACAM in the step e), the AM extractor/generator generates the ACAM by a method using an agree-all model or a method using a voting model.

9. The method according to claim 8, wherein the method using the agree-all model sets each of analysis conditions of the plurality of analysis models to a specific predicted probability value.

10. The method according to claim 9, wherein the method using the voting model sets each of the analysis conditions of the plurality of analysis models to a specific predicted probability value different from the specific predicted probability value in the method using the agree-all model.

11. The method according to claim 7, further comprising selecting, by a representative image selector, a representative image through measurement of a similarity with respect to the ACAM after the step e).

12. The method according to claim 11, wherein, when the representative image selector selects the representative image, an output probability of a frame having a highest similarity is used as a probability of the representative image, or an output probability average value of representative image candidates greater than or equal to a threshold is used as the probability of the representative image.

13. A method of visualizing an analysis result of an endoscopic image, the method comprising steps of:
   a) loading, by a model loading/condition setting unit, a plurality of analysis models and setting analysis conditions of the analysis models;
   b) determining, by an image analyzer, whether a situation requires image analysis, and reading an image frame when the situation requires image analysis;
   c) determining, by the image analyzer, whether a mode is a detection mode or a classification mode, analyzing the image in the detection mode when the mode is the detection mode, and analyzing the image in the classification mode when the mode is the classification mode;
   d) determining, by an AM extractor/generator, whether an image analysis result by the image analyzer satisfies an analysis condition set by the model loading/condition setting unit;
   e) extracting, by the AM extractor/generator, AMs of the plurality of analysis models when the analysis condition is satisfied in the determining of the step d) and generating a CAM based on the extracted AMs;
   f) determining, by the AM extractor/generator, whether an analysis target is detected in a previous image frame and generating an ACAM by applying weights to CAMs extracted in the previous image frame and a current image frame when the analysis target is detected;
   g) extracting, by an activation value extractor, a peak activation value from the ACAM generated by the AM extractor/generator;
   h) determining, by a closed curve extractor, whether the extracted peak activation value is greater than or equal to a detection confirmation threshold, extracting a closed curve of an AM when the extracted peak activation value is greater than or equal to the detection confirmation threshold, and drawing the closed curve on a corresponding analysis image; and
   i) determining, by the image analyzer, whether to change an analysis mode, and changing the analysis mode to the classification mode when a current analysis mode is the detection mode and changing the analysis mode to the detection mode when the current analysis mode is the classification mode in a case of changing the analysis mode.

14. The method according to claim 13, wherein when the AM extractor/generator generates the ACAM in the step f), the AM extractor/generator generates the ACAM by a method using an agree-all model or a method using a voting model.

15. The method according to claim 14, wherein the method using the agree-all model sets each of analysis conditions of the plurality of analysis models to a specific predicted probability value.

16. The method according to claim 15, wherein the method using the voting model sets each of the analysis conditions of the plurality of analysis models to a specific predicted probability value different from the specific predicted probability value in the method using the agree-all model.

17. The method according to claim 13, further comprising selecting, by a representative image selector, a representative image through measurement of a similarity with respect to the ACAM after the step r).

18. The method according to claim 17, wherein, when the representative image selector selects the representative image, an output probability of a frame having a highest similarity is used as a probability of the representative image, or an output probability average value of representative image candidates greater than or equal to a threshold is used as the probability of the representative image.

* * * * *